United States Patent [19]

Carletti et al.

[11] Patent Number: 5,500,285
[45] Date of Patent: Mar. 19, 1996

[54] REACTIVE FLAME RETARDANT ADDITIVES CONTAINING PHOSPHINO OXIDE MOIETIES

[75] Inventors: Vittorio Carletti, Novara; Gianfranco Longhini, Vercelli; Riccardo Po', Livorno; Roberto Podesta', Lomagna; Anna M. Romano, Novara; Cecilia Querci, Novara, all of Italy

[73] Assignees: Great Lakes Chemical Italia S.r.l.; Eniricerche S.p.A., both of Milan, Italy

[21] Appl. No.: 373,441

[22] Filed: Jan. 17, 1995

[30] Foreign Application Priority Data

Jan. 20, 1994 [IT] Italy ................... MI94A0070

[51] Int. Cl.⁶ .................................. D02G 3/00
[52] U.S. Cl. .................. 428/364; 528/272; 528/287; 528/289; 528/298; 528/302; 528/308; 528/308.6; 528/398; 525/437
[58] Field of Search .................. 528/44, 65, 66, 528/272, 287, 289, 298, 302, 308, 308.6, 398; 525/437; 428/364

[56] References Cited

U.S. PATENT DOCUMENTS

| | | | |
|---|---|---|---|
| 4,073,829 | 2/1978 | Moedritzer | 525/437 |
| 4,181,646 | 1/1980 | Moedritzer | 524/126 |
| 4,383,049 | 5/1983 | Blount | 521/135 |
| 4,935,304 | 6/1990 | Danforth | 428/423.1 |
| 5,077,337 | 12/1991 | Atwell et al. | 525/72 |

FOREIGN PATENT DOCUMENTS

| | | |
|---|---|---|
| 0096799 | 12/1983 | European Pat. Off. |
| 3521125 | 12/1986 | Germany |
| 3544064 | 6/1987 | Germany |

*Primary Examiner*—Samuel A. Acquah
*Attorney, Agent, or Firm*—Oblon, Spivak, McClelland, Maier & Neustadt

[57] ABSTRACT

Phosphino oxide group containing compounds useful as flame retardant additives, having the general formula (I):

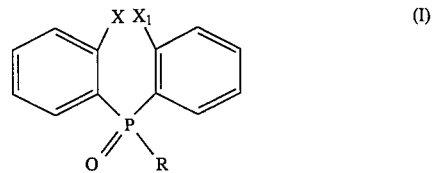

wherein:

X and $X_1$ represent a hydrogen atom or, when taken jointly, they represent an $NR_1$ moiety in which $R_1$ stands for a hydrogen atom; a linear or branched aliphatic $C_1$–$C_5$ moiety; a linear or branched $C_2$–$C_6$ acyl moiety; a phenyl moiety;

R represents a cyclic or polycyclic $C_4$–$C_9$ moiety containing two carboxy groups, possibly esterified with univalent alcohols or glycols, or transformed into anhydrides, or two hydroxy groups.

8 Claims, No Drawings

REACTIVE FLAME RETARDANT ADDITIVES CONTAINING PHOSPHINO OXIDE MOIETIES

The present invention relates to novel compounds containing phosphino oxide groups.

More particularly, the present invention relates to compounds containing phosphino oxide groups, to a process for preparing them, and to their use as flame retardant additives for organic polymers.

In the art of organic polymers, the need exists for having available flame resistant articles of manufacture, in particular in some sectors, e.g., in the textile sector.

In order to endow organic polymer with flame resistance properties (i.e., to "flame retard" them), several flame retardant additives are used which, in general, are organic compounds containing halogens or phosphorus, to be applied by means of a surface treatment of the article of manufacture, e.g., in a textile material finishing step.

Flame retardant additives constituted by organic compounds containing phosphorus and/or halogen, or halogenated compounds, in combination with a metal oxide are described, e.g., by J. W. Lyons in "The Chemistry and Uses of Fire Retardants", Wiley Interscience 1970, pp. 286–297.

The present Applicant has found now novel compounds containing phosphino oxide groups, useful as flame retardant additives, which are capable of being incorporated, as comonomers, with the polymer to be flame retarded.

Such compounds, useful as flame retardant additives for organic polymers such as, e.g., polyesters or polyurethanes, allow the drawbacks which affect the prior art to be overcome, because:

no corrosive fumes as, e.g., hydrogen halide acids, are released (on the contrary, such gases are formed during the combustion of halogen containing additives);

they contain analogous functional groups to those present in the monomers of the polymer to be admixed and therefore they do not considerably alter the polymerization reaction, because they are capable of partially replacing them;

they do not form complexes with the polymerization catalysts and, therefore, can be added during the initial reaction stage, thus simplifying the process;

they display a high heat and chemical stability and, consequently, they do not undergo any undesired alterations due to the harsh reaction conditions under which the polymer synthesis step is carried out;

they do not undergo migrations to the outside of the polymeric matrix, because they make a part of the same polymeric chain, thus securing the absence of contamination of food or other goods put into contact with the end article of manufacture and furthermore securing that their flame retardant action will not decrease in the event of a decrease in their concentration in the polymer.

Therefore, the subject-matter of the present invention are compounds containing phosphino oxide groups having general formula (I):

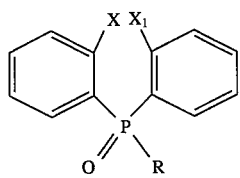

(I)

wherein:

X and $X_1$ represent a hydrogen atom or, when they are taken jointly, they represent an $NR_1$ moiety in which $R_1$ stands for a hydrogen atom; a linear or branched aliphatic $C_1$–$C_5$ moiety; a linear or branched $C_2$–$C_6$ acyl moiety; a phenyl moiety;

R represents a cyclic or polycyclic $C_4$–$C_9$ moiety containing two carboxy groups, possibly esterified with univalent alcohols or glycols, or transformed into anhydrides, or two hydroxy groups.

The compounds having general formula (I) are useful as flame retardant additives.

Preferred compounds having general formula (I) are those in which:

X and $X_1$ represent a hydrogen atom or, when they are taken jointly, they represent an —NH— moiety;

R represents a moiety derived from cyclohexane or norbornane containing two methylol groups or a dianhydride group or two carboxy groups esterified with methanol.

Specific examples of compounds having general formula (I) are:

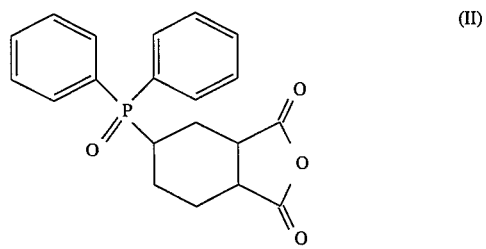

(II)

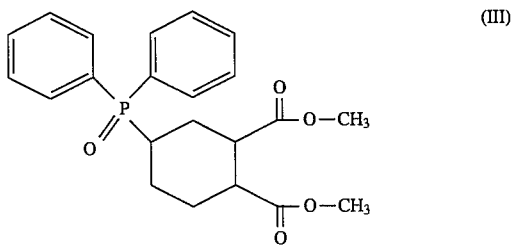

(III)

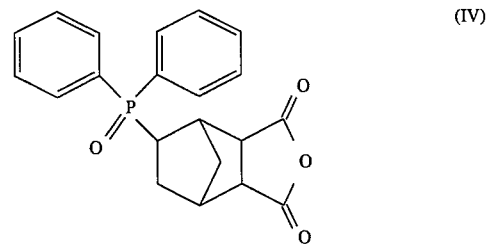

(IV)

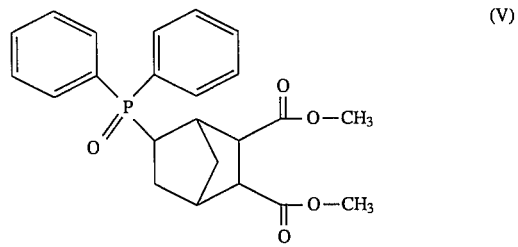

(V)

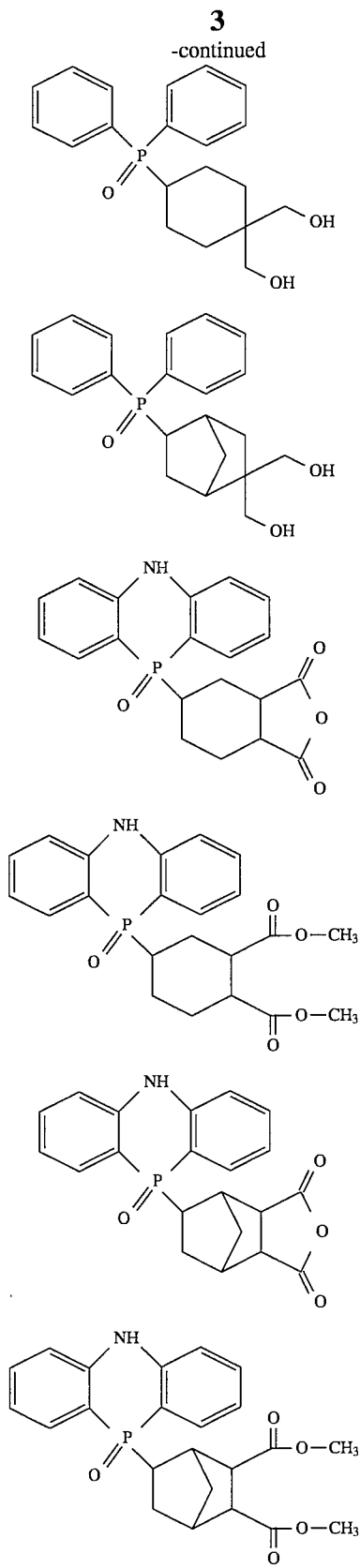

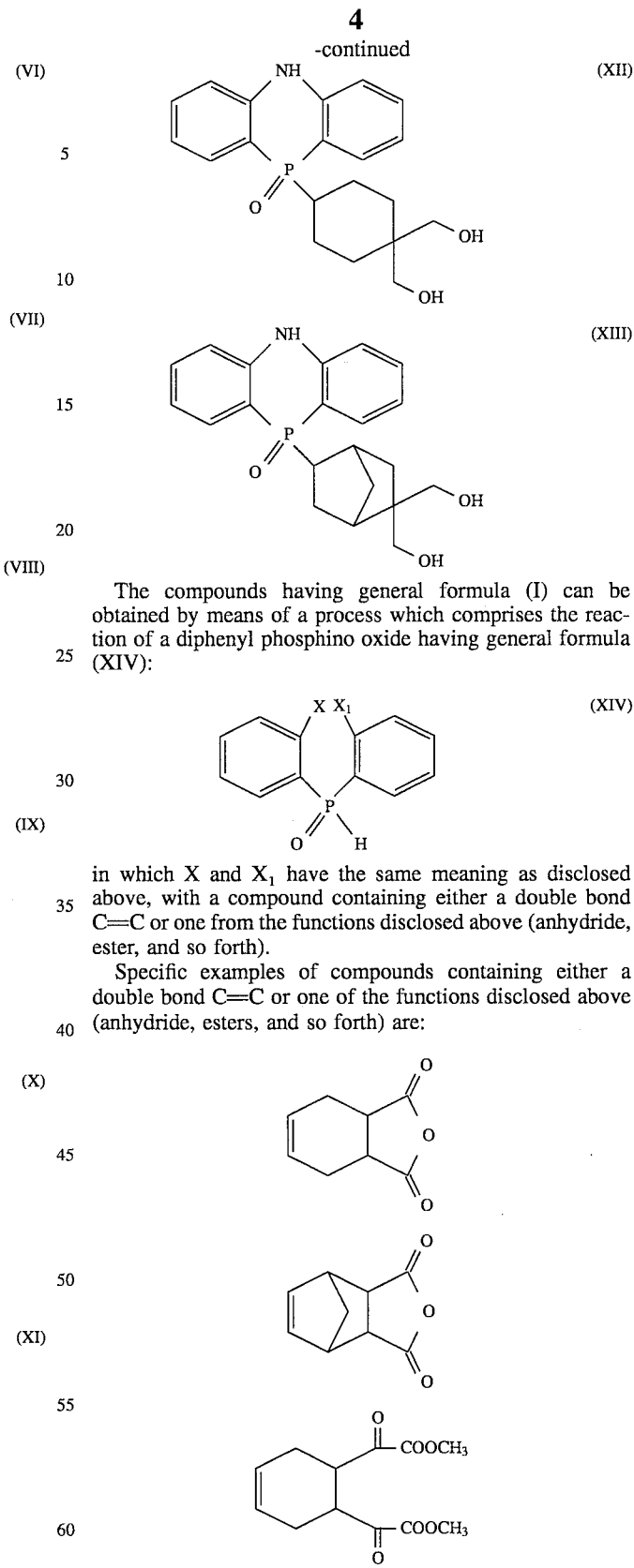

The compounds having general formula (I) can be obtained by means of a process which comprises the reaction of a diphenyl phosphino oxide having general formula (XIV):

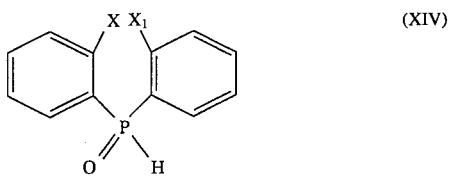

in which X and $X_1$ have the same meaning as disclosed above, with a compound containing either a double bond C=C or one from the functions disclosed above (anhydride, ester, and so forth).

Specific examples of compounds containing either a double bond C=C or one of the functions disclosed above (anhydride, esters, and so forth) are:

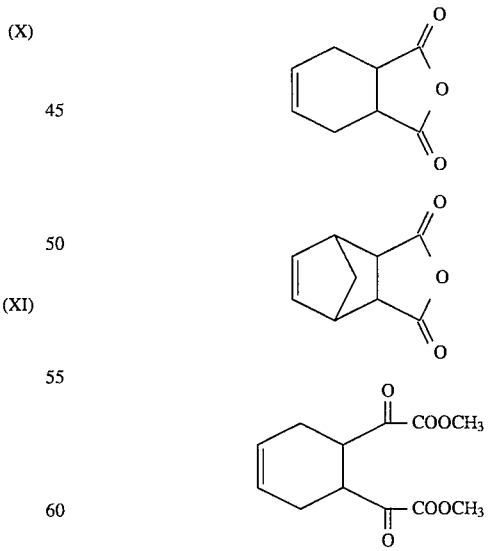

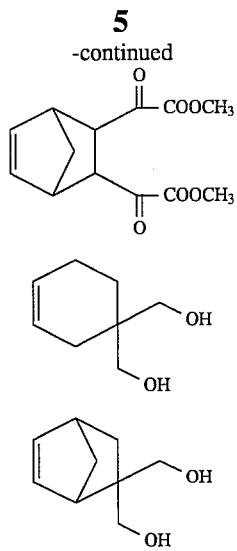

The diphenyl phosphino oxide having general formula (XIV) is prepared according to known processes described in the art, such as, e.g., in Haake et al., (1969), Journal of Organic Chemistry, Vol. 34, pp. 788–794.

Those compounds which contain either a double bond C=C or one of the functions disclosed above (anhydride, ester, and so forth), some examples of which are reported above, are commercial products.

The reaction is carried out according to known modalities as described, e.g., by Dolidze A. V., Ingorokva K. V. et al., in: "Izvestiya Akademii Nauk Gruzinoskoi SSR, Seriya Khimicheskaya" (1987), Vol. 13(4), pp. 309–311 and Ninfant'ev E. E., Magdeeva R. K. et al. in: "Zhurnal Obshchei Khimii" (1968), Vol. 56(7), pp. 1660–1661.

The compounds having general formula (I) according to the present invention are useful as flame retardant additives, suitable for endowing organic polymers such as, e.g., linear polyesters with aliphatic and/or aromatic structures (PET, PBT, and so forth), polyurethanes, and so forth, with characteristics of flame resistance.

The compounds having general formula (I) are mixed and homogenized with the monomers from which the polymer is being produced, at the beginning of the polymerization reaction, because, as already stated hereinabove, they do not form complexes with the reaction catalysts.

The so obtained end product can be subsequently be transformed into manufactured articles as fibres, films, moulded articles, and so forth.

The compounds having general formula (I) according to the present invention are capable of reacting with the polymer to which they are added, becoming a part of the same polymer and thus endowing it with flame retardant characteristics. They are furthermore capable of remaining overtime inside the interior of the polymeric material they are incorporated with.

For example, in the case of poly(ethylene terephthalate) (PET) or of poly(butylene terephthalate) (PBT), those hydroxy function containing compounds having formulae (VI), (VII), (XII) and (XIII), can replace an equivalent number of mols of glycol; those anhydride function containing compounds (II), (IV), (VIII) and (X), can replace an equivalent number of mols of terephthalic acid and the diester function containing compounds can replace an equivalent number of mols of methyl terephthalate, in the case when the polyester synthesis process will start from this compound, instead than from the free acid.

The amount of compounds having general formula (I) using to provide flame retardant characteristics is that amount which secures a phosphorus content (calculated as elemental phosphorus) in the organic polymer comprised within the range of from 0.1% to 3% by weight, preferably from 0.4% to 0.7% by weight.

The compounds having general formula (I) according to the present invention were characterized by $^1$H-NMR and $^{31}$P-NMR spectrometry in $CDCl_3$, using a BRÜKER-AC-200 spectrometer and by mass spectrometry by the DCI method (chemical ionization with isobutane as the reactant gas), using a FINNIGAN MAT 8004 spectrometer. The following experimental examples are reported in order to illustrate the present invention without limiting it.

EXAMPLE 1

Preparation of Compound Having Formula (II)

To a 3-necked flask of 500 cm$^3$ of capacity equipped with condenser, thermometer, magnetic stirring means and fitting for inert gas flow, 7.6 g (0.05 mol) of tetrahydrophthalic anhydride; 10.1 g (0.05 mol) of diphenyl phosphino oxide and 0.41 g (0.025 mol) of azoisobutyronitrile (AIBN) are charged.

After heating the mixture at 80° C. during 6 hours under a nitrogen flow, from the $^{31}$P-NMR spectrum obtained from the raw reaction mixture, a singlet at 36.5 ppm with an integral value of 90%, is evidenced.

The reaction temperature is then decreased down to 40° C., 30 ml of ethyl ether is added and the white solid precipitate is filtered and dried.

An amount of 12.5 g of product is obtained, in a yield of 71%, which is further purified, in order to remove any traces of diphenyl phosphino oxide, by recrystallization from toluene or, preferably, from 1,2-dichloroethane, with, in the latter case, a purity of >99.9% being obtained.

An end amount of 10 g (yield 57%) is obtained of product displaying the following characteristics:

Melting point: 210° C.–215° C.

$^1$H-NMR (200 MHz, CDCl$_1$-TMS) (ppm): 7.6–7.1 (10H, m); 3.3 (2H, m); 2.4 (1H, t); 2.0 (2H, m); 1.5 (2H, m); 1.1 (2H, m).

$^{31}$P: 36.5 ppm (s).

IR: 3050 cm$^{-1}$ (aromatic CH), 1880 cm$^{-1}$ (anhydride C=O); 1130 cm$^{-1}$ (P=O).

Mass (ms): 354 m/z (molecular peak).

EXAMPLE 2

Preparation of Compound Having Formula (IV)

To a 3-necked flask of 250 cm$^3$ of capacity equipped with condenser, thermometer, magnetic stirring means and fitting for inert gas flow, 21.93 g (0.1336 mol) of anhydride of cis-5-norbornene-endo- 2,3-dicarboxy acid, 27.0 g (0.1336 mol) of diphenyl phosphino oxide, 50 cm$^3$ of toluene and 1.1 g (0.067 mol) of azoisobutyronitrile (AIBN) are charged.

The mixture is heated up to 80° C. under a nitrogen flow and is kept at that temperature during 2 hours. The temperature is then increased up to 90° C. and the reaction is continued during a further 4 hours with 0.2 g of benzoyl peroxide being added every hour.

The progress of the reaction can be monitored by TLC (0.25 mm Kieselgel 60 F$_{254}$), using, as eluent, 2:8 methanol:ethylether. The results obtained from TLC are reported in following Table 1:

TABLE 1

| Product | r.f.* | U.V. Detection | KMnO$_4$ Detection |
|---|---|---|---|
| Diphenyl phosphino oxide | 0.95 | YES | YES |
| Anhydride | 0.80–0.50 (band) | NO | YES |
| Product (IV) | 0.70 | YES | NO |

*r.f. = ratio of the distance run by the spot to the distance run by eluent front.

When reaction is complete, the reaction mixture is cooled and is allowed to stand at 4° C. The white solid precipitate is filtered, washed with toluene and dried.

An amount of 21 g (yield 43%) is obtained of product with a glassy appearance, which is further purified in order to remove any traces of diphenyl phosphino oxide, by recrystallizing it from toluene or, preferably, from 1,2-dichloroethane, with, in the latter case, a purity of >99.9% being obtained.

At the end 13.2 g of product, having the following characteristics:

Melting point: 195° C.–197° C.

Mass (ms): 366 m/z (molecular peak) is obtained in a yield of 30%.

EXAMPLE 3

Preparation of Compound Having Formula (VI)

27.93 g (0.1336 mol) of 1,1-dimethylol-cyclohex-3-ene; 27.0 g (0.1336 mol) of diphenyl phosphino oxide; 50 cm$^3$ of toluene and 1.1 g (0.067 mol) of azoisobutyronitrile (AIBN) are charged to a 3-necked flask of 250 cm$^3$ of capacity equipped with condenser, thermometer, magnetic stirring means and fitting for inert gas flow.

The reaction mixture is heated, under nitrogen flow, at 80° C., and this temperature is kept during 2 hours.

After 1 hour, a white solid starts to precipitate. The temperature is then increased up to 90° C. and the reaction is continued for a further 4 hours with 0.2 g of benzoyl peroxide being added every hour.

At the end of the reaction, the reaction mixture is cooled and is allowed to stand at 4° C. The white solid precipitate is filtered, washed with acetone and dried.

An amount of 42 g (yield 76%) is obtained of product which is further purified, in order to remove any traces of diphenyl phosphino oxide, by recrystallization from toluene.

At the end, 33.5 g of product having the following characteristics:

Melting point: 162° C.–166° C.

Mass (ms): 344 m/z (molecular peak) is obtained in a yield of 61%.

From analysis by HPLC on a Licrospher 100 RP/8 (5 μm diameter) column using, as eluent, a mixture of water: acetonitrile in a variable ratio, the presence of at least two products having the same molecular weight is observed. These are supposed to be the isomers with phosphorus bonded in either 3- or 4-position to the geminal methylol groups.

EXAMPLE 4

Preparation of Compound Having Formula (VII)

9.22 g (0.06 mol) of 1,1-dimethylolnorbornene; 12.1 g (0.06 mol) of diphenyl phosphino oxide; 50 cm$^3$ of toluene and 0.5 g (0.030 mol) of azoisobutyronitrile (AIBN) are charged to a flask of 100 cm$^3$ of capacity equipped with condenser, thermometer, magnetic stirring means and fitting for inert gas flow.

The reaction mixture is heated, under nitrogen flow, up to 80° C., and is kept at that temperature during 2 hours.

After 1 hour, a white solid starts to precipitate. The reaction temperature is kept at 80° C.– 85° C. and the reaction is continued for a further 4 hours with 0.1 g of benzoyl peroxide being added every hour.

At the end of the reaction, after cooling, 50 cm$^3$ of acetone is added to the flask and the mixture is stirred, still when cold, during approximately 15 minutes.

The reaction mixture is filtered and the precipitate is washed with acetone, with 19 g (yield 89%) being thus obtained of product, which is furthermore purified, in order to remove any traces of diphenyl phosphino oxide, by recrystallization from toluene.

At the end, 15.4 g of product having the following characteristics:

Melting point: 173° C.–175° C.

Mass (ms): 356 m/z (molecular peak) is obtained in a yield of 72%.

From analysis by HPLC on a Licrospher 100 RP/8 (5 μm diameter) column using, as eluent, a mixture of water: acetonitrile in a variable ratio, the presence of at least two products having the same molecular weight is observed. These are supposed to be the isomers with phosphorus bonded in either 3- or 4-position to the geminal methylol groups.

EXAMPLE 5

Preparation of poly(ethylene terephthalate) Containing the Compound Having Formula (II)

97.0 g (0.50 mol) of dimethyl terephthalate; 68.0 g (1.10 mol) of ethylene glycol and 100 mg of manganese acetate [Mn(CH$_3$COO$_2$.4H$_2$O] are charged to a glass flask of 500 ml of capacity.

The reaction mixture is purged, air inside the flask is replaced by an inert atmosphere (nitrogen) and the reaction is heated up to 180° C. on a sand bath. The temperature of the sand bath is kept at 180° C. until methanol is nearly totally distilled and the reaction temperature is subsequently gradually increased up to 230° C.–240° C.

Now, a suspension of 64 mg of antimony trioxide, 250 mg of triphenyl phosphate and 7.1 g of compound having formula (II) in glycol is added.

The pressure is decreased down to about 300 torr in order to remove any traces of methanol and ethylene glycol. Approximately 30 minutes later, the pressure is reduced down to 0.2 torr and the temperature is simultaneously increased up to 280° C.–285° C.

As soon as the polymer reaches such a viscous consistency as to indicate that a high molecular weight is reached, the reaction flask is removed from the sand bath it was in, and is dipped into liquid nitrogen.

The polymer is finally recovered and pelletized.

The so obtained polymer displays a LOI (Limited Oxigen Index) of 25, whilst additive-free polyethylene terephthalate displays an LOI of 20. LOI determination is carried out according to ASTM D 2863-77.

We claim:

1. A compound containing phosphino oxide groups, of formula (I):

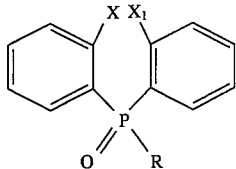

wherein

X and $X_1$ represent a hydrogen atom, or taken together represent an $NR_1$ moiety in which $R_1$ represents a hydrogen atom, a linear or branched $C_{1-5}$ aliphatic moiety, a linear or branched $C_{2-6}$ acyl moiety or phenyl moiety;

R represents a $C_{4-9}$ cyclic or polycyclic moiety containing two carboxyl groups, $C_{4-9}$ cyclic or polycyclic moiety containing two carboxyl groups esterified with univalent alcohols or glycols, a $C_{4-9}$ cyclic or polycyclic moiety containing two carboxyl groups transformed into anhydrides, or two hydroxy groups.

2. A flame retardant composition comprising a compound containing phosphino oxide groups, of formula (I):

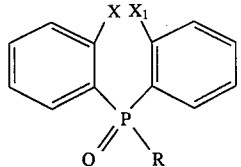

wherein

X and $X_1$ represent a hydrogen atom, or taken together represent an $NR_1$ moiety in which $R_1$ represents a hydrogen atom, a linear or branched $C_{1-5}$ aliphatic moiety, a linear or branched $C_{2-6}$ acyl moiety or phenyl moiety;

R represents a $C_{4-9}$ cyclic or polycyclic moiety containing two carboxyl groups, $C_{4-9}$ cyclic or polycyclic moiety containing two carboxyl groups esterified with univalent alcohols or glycols, a $C_{4-9}$ cyclic or polycyclic moiety containing two carboxyl groups transformed into anhydrides, or two hydroxy groups.

3. The flame retardant composition of claim 2, wherein X and $X_1$ represent a hydrogen atom or taken together represent an —NH— moiety;

R represents a moiety derived from cyclohexane or norbornane containing two methylol groups or a dianhydride group or two carboxy groups esterified with methanol.

4. A flame retarded organic polymer comprising:

i) a polymer selected from the group consisting of a linear polyester with an aliphatic structure, a linear polyester with an aromatic structure and a linear polyester with aliphatic and aromatic structures; and ii) a compound of formula (I)

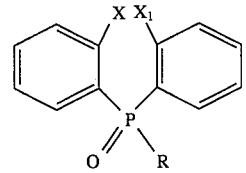

wherein

X and $X_1$ represent a hydrogen atom, or taken together represent an $NR_1$ moiety in which $R_1$ represents a hydrogen atom, a linear or branched $C_{1-5}$ aliphatic moiety, a linear or branched $C_{2-6}$ acyl moiety or phenyl moiety;

R represents a $C_{4-9}$ cyclic or polycyclic moiety containing two carboxyl groups, $C_{4-9}$ cyclic or polycyclic moiety containing two carboxyl groups esterified with univalent alcohols or glycols, a $C_{4-9}$ cyclic or polycyclic moiety containing two carboxyl groups transformed into anhydrides, or two hydroxy groups wherein said compound of formula (I) is mixed and homogenized with the monomers of said organic polymer at the beginning of the polymerization reaction.

5. The flame retarded organic polymer of claim 4, wherein the amount of phosphorous, calculated as elemental phosphorous, is from 0.1 to 3% by weight based on the weight of organic polymer.

6. A fiber, film, or molded article comprising the organic polymer of claim 4.

7. Flame retarded organic polymers according to claim 4, in which the polyester is poly(ethylene terephthalate).

8. Flame retarded organic polymers according to claim 4, in which the polyester is poly(butylene terephthalate).

* * * * *